US012778525B2

(12) United States Patent
Lee

(10) Patent No.: US 12,778,525 B2
(45) Date of Patent: Nov. 3, 2026

(54) PORTABLE X-RAY IMAGING DEVICE

(71) Applicant: ELEC-FIELD FUTURE CORP., Gyeonggi-do (KR)

(72) Inventor: Han Sung Lee, Gyeonggi-do (KR)

(73) Assignee: ELEC-FIELD FUTURE CORP., Gyeonggi-do (KR)

( * ) Notice: Subject to any disclaimer, the term of this patent is extended or adjusted under 35 U.S.C. 154(b) by 304 days.

(21) Appl. No.: 18/485,685

(22) Filed: Oct. 12, 2023

(65) Prior Publication Data

US 2025/0099053 A1 Mar. 27, 2025

(30) Foreign Application Priority Data

Sep. 27, 2023 (KR) ........................ 10-2023-0130438

(51) Int. Cl.
*A61B 6/00* (2024.01)
*A61B 90/00* (2016.01)

(52) U.S. Cl.
CPC ...... *A61B 6/4405* (2013.01); *A61B 2090/365* (2016.02); *A61B 2090/371* (2016.02)

(58) Field of Classification Search
CPC ............ A61B 6/4405; A61B 2090/365; A61B 2090/371
See application file for complete search history.

(56) References Cited

U.S. PATENT DOCUMENTS

2008/0259336 A1* 10/2008 Konno .................... G01J 3/508 356/404
2009/0092948 A1* 4/2009 Gantes ................... A61C 1/084 433/215
2009/0114825 A1* 5/2009 Beekman ............. G01T 1/1642 250/362
2009/0136000 A1* 5/2009 Nishii ...................... A61B 6/08 378/98.3
2013/0162796 A1* 6/2013 Bharara ................. A61B 5/015 348/77
2013/0286174 A1* 10/2013 Urakabe .................. A61B 1/04 348/66
2014/0050298 A1* 2/2014 Lee ........................ A61B 6/512 378/39
2014/0285647 A1* 9/2014 Okusu ................... G06T 7/0014 348/77
2015/0036025 A1* 2/2015 Oshima .................. G03B 13/06 348/239

(Continued)

FOREIGN PATENT DOCUMENTS

KR 20090053568 A * 5/2009 ........... A61B 6/4405
KR 10-2015-0057013 A 5/2015

(Continued)

*Primary Examiner* — Blake C Riddick
(74) *Attorney, Agent, or Firm* — IP Legal Services, LLC

(57) ABSTRACT

The present disclosure relates to a portable X-ray imaging device. The portable X-ray imaging device includes an optical camera, a thermal image camera, a display unit, and a controller. The controller displays a real image captured by the optical camera and a thermal image captured by the thermal image camera by overlapping the real image and the thermal image. Accordingly, a user can perform more accurate X-ray imaging because the user can check an oral sensor in a real image of the face of a patient displayed on the display unit.

14 Claims, 5 Drawing Sheets

(56) References Cited

U.S. PATENT DOCUMENTS

| | | | | |
|---|---|---|---|---|
| 2015/0110246 | A1* | 4/2015 | Liu | A61B 6/461<br>378/62 |
| 2015/0238287 | A1* | 8/2015 | Pulido | A61B 1/247<br>356/601 |
| 2016/0135904 | A1* | 5/2016 | Daon | A61B 5/064<br>600/424 |
| 2016/0278731 | A1* | 9/2016 | Babic | A61B 90/39 |
| 2016/0361035 | A1* | 12/2016 | Lee | A61B 6/469 |
| 2017/0333294 | A1* | 11/2017 | Brown | A61B 5/0086 |
| 2018/0070911 | A1* | 3/2018 | Franklin | A61B 6/40 |
| 2018/0116524 | A1* | 5/2018 | Aoshima | A61B 6/4452 |
| 2018/0116623 | A1* | 5/2018 | Inoue | A61B 6/547 |
| 2018/0339720 | A1* | 11/2018 | Singh | G06T 7/001 |
| 2019/0046130 | A1* | 2/2019 | Imamura | H05G 1/60 |
| 2019/0046134 | A1* | 2/2019 | Imamura | A61B 6/465 |
| 2019/0046135 | A1* | 2/2019 | Hattori | G06V 10/143 |
| 2019/0053771 | A1* | 2/2019 | Butani | A61B 6/502 |
| 2019/0110768 | A1* | 4/2019 | Lee | A61B 6/54 |
| 2019/0231492 | A1* | 8/2019 | Sabina | A61B 1/0638 |
| 2019/0269485 | A1* | 9/2019 | Elbaz | A61B 1/00193 |
| 2019/0365237 | A1* | 12/2019 | Lee | H04N 23/695 |
| 2019/0371014 | A1* | 12/2019 | Etoh | G01D 7/00 |
| 2020/0237452 | A1* | 7/2020 | Wolf | G06F 3/048 |
| 2020/0273581 | A1* | 8/2020 | Wolf | G16H 40/63 |
| 2020/0301248 | A1* | 9/2020 | Shimizu | G03B 13/06 |
| 2020/0326705 | A1* | 10/2020 | Appel | B08B 9/051 |
| 2020/0330062 | A1* | 10/2020 | Lee | A61B 6/465 |
| 2021/0137634 | A1* | 5/2021 | Lang | A61B 90/00 |
| 2021/0169438 | A1* | 6/2021 | Ruff | A61B 6/547 |
| 2022/0076612 | A1* | 3/2022 | Nagao | G09G 3/20 |
| 2022/0121854 | A1* | 4/2022 | Bourn | H04N 23/30 |
| 2023/0031298 | A1* | 2/2023 | Imaizumi | H04N 23/6812 |
| 2023/0034478 | A1* | 2/2023 | Benson | A61B 5/7425 |
| 2023/0034538 | A1* | 2/2023 | Ishibashi | H04N 23/6842 |
| 2023/0035277 | A1* | 2/2023 | Imaizumi | H04N 23/667 |
| 2023/0039343 | A1* | 2/2023 | Ruff | A61B 6/463 |
| 2023/0165454 | A1* | 6/2023 | Ohtsuka | A61C 9/0053<br>433/29 |
| 2023/0270395 | A1* | 8/2023 | Ruff | A61B 6/5247<br>378/98.2 |
| 2023/0301609 | A1* | 9/2023 | Ruff | A61B 6/032 |
| 2023/0308613 | A1* | 9/2023 | Okuhara | G06T 5/80 |
| 2024/0112439 | A1* | 4/2024 | Sugahara | G06V 40/103 |
| 2024/0277231 | A1* | 8/2024 | Takahashi | A61B 5/0077 |
| 2025/0073003 | A1* | 3/2025 | Fridman | G16H 30/20 |

FOREIGN PATENT DOCUMENTS

| | | | |
|---|---|---|---|
| KR | 10-2020-0061143 | A | 6/2020 |
| KR | 10-2022-0049302 | A | 4/2022 |
| KR | 10-2023-0001737 | A | 1/2023 |
| KR | 10-2578414 | B1 | 9/2023 |

* cited by examiner

PORTABLE X-RAY IMAGING DEVICE

CROSS REFERENCE TO PRIOR APPLICATIONS

The present application claims priority under 35 U.S.C. § 119 to Korean Patent Application No. 10-2023-0130438 (filed on Sep. 27, 2023).

BACKGROUND

1. Technical Field

The present disclosure relates to a portable X-ray imaging device, and more particularly, to a portable X-ray imaging device which enables a user to perform X-ray imaging while holding the portable X-ray imaging device in hand and freely changing the imaging location and posture of the portable X-ray imaging device.

2. Related Art

In general, X-ray imaging equipment that is used in a hospital is used with its installation location not changed because the X-ray imaging equipment is large in size and heavy in weight. Such equipment has disadvantages in that it occupies a wide installation space and has a low degree of freedom in a change in the imaging location and posture of the portable X-ray imaging device.

Accordingly, there was developed a portable X-ray imaging device having a size and weight, which enable a user to perform X-ray imaging while holding the portable X-ray imaging device in hand and freely changing his or her location.

The portable X-ray imaging device is mostly usefully used to image teeth X-ray in a dental hospital.

A shielding plate that includes a lead oxide material in order to block backward scattering of X-rays, that is semi-transparent, and that has an approximately disc form is disposed in a rear part of the portable X-ray imaging device at a predetermined distance from a front end thereof. There is a problem in that a user's field of view is blocked by the shielding plate when an oral sensor and the portable X-ray imaging device are aligned in order to perform X-ray imaging.

For this reason, there has recently been developed a portable handheld type X-ray imaging device that includes an optical camera and a display unit and that has solved the phenomenon in which a user's field of view is blocked by the shielding plate by displaying a front image of the portable X-ray imaging device on the display unit.

In a dental hospital, when the inside of the mouth of a patient is imaged by using the portable X-ray imaging device, an X-ray sensing plate called an intraoral X-ray sensor is also used. The intraoral X-ray sensor is disposed within the mouth. The portable X-ray imaging device performs X-ray imaging in a way to radiate X-rays from the outside of the face of the patient toward the oral sensor.

However, a user (i.e., a person who performs X-ray imaging) performs X-ray imaging in the state in which the user guesses the location of the oral sensor by his or her senses because the oral sensor disposed within the mouth of the patient is not seen to the outside as described above. Accordingly, there is a problem in that an accurate X-ray image at a desired location cannot be obtained if an X-ray radiation direction is not accurate. That is, conventionally, there is a disadvantage in that obtaining a mouth X-ray photo at an accurate location is greatly affected by user proficiency.

A conventional technology is technical information that has been owned by an inventor in order to derive the present disclosure or that is obtained in a process of deriving the present disclosure, and may not be said to be a known technology that has been disclosed to the common public prior to the application of the present disclosure.

PRIOR ART DOCUMENT

Patent Document (Patent Document 1) Korean Patent Application Publication No. 10-2023-0001737 (laid open on Jan. 5, 2023)

SUMMARY

Various embodiments are directed to providing a portable X-ray imaging device capable of more accurately imaging a desired location by accurately radiating X-rays toward an oral sensor.

Technical objects to be achieved by the present disclosure are not limited to the aforementioned object, and the other objects not described above may be evidently understood from the following description by a person having ordinary knowledge in the art to which the present disclosure pertains.

In an embodiment, a portable X-ray imaging device includes a main body in which an X-ray radiation window has been disposed at a front end thereof, an X-ray source installed within the main body, an optical camera installed on an outer circumference of the front end on one side of the main body and configured to capture a real image of a subject, a thermal image camera installed adjacently to the optical camera and configured to capture a thermal image of the subject, a display unit installed on the top of the main body and configured to display the real and thermal images captured by the optical camera and the thermal image camera, and a controller configured to control operations of the X-ray source, the optical camera, the thermal image camera, and the display unit.

The optical camera and the thermal image camera are installed at an upper center of the circumference of the front end of the main body.

The optical camera and the thermal image camera are installed in the state in which the optical camera and the thermal image camera have an installation angle $\alpha$ at which the optical camera and the thermal image camera have been forward inclined with respect to a surface perpendicular to a direction in which the X-ray source radiates X-rays.

The installation angle $\alpha$ is in a range of more than 0° to less than 30°.

The display unit may display the real image captured by the optical camera without any change.

The display unit may display the thermal image captured by the thermal image camera without any change.

The controller may generate an overlap image by overlapping the real image captured by the optical camera and the thermal image captured by the thermal image camera. The display unit may display the overlap image.

The optical camera may generate data of the real image obtained by capturing a face of a patient who has an oral sensor in his or her mouth. The thermal image camera may generate data of the thermal image obtained by capturing the face of the patient who has the oral sensor in his or her mouth. The controller may generate the overlap image in which the oral sensor has been displayed in the real image of the face of the patient by overlapping the real image of the face of the patient and the thermal image of the face of the patient, based on the data of the real image and the data of the thermal image which have been obtained by capturing the face of the patient who has the oral sensor in his or her mouth. The display unit may display the overlap image in which the oral sensor has been displayed in the real image of the face of the patient.

The controller may overlap the real image of the face of the patient and the thermal image of the face of the patient after reducing resolution of the real image and the thermal image.

The controller may overlap the real image of the face of the patient and the thermal image of the face of the patient, in a way to specify a plurality of points in the real image of the face of the patient, specify a plurality of identical points corresponding to the plurality of specified points in the thermal image of the face of the patient, and match the plurality of points of the real image and the plurality of points of the thermal image.

The plurality of points may be three points corresponding to a central point between both eyes of the patient and the peak of the nose of the patient.

The controller may overlap the real image in an original state and the thermal image the remaining part of which has been processed to be transparent except the part of the oral sensor in the original state.

The controller may display the part of the oral sensor in a specific color.

The controller may display an outer contour in the part of the oral sensor.

As described above, the portable X-ray imaging device according to an embodiment of the present disclosure has an effect in that it can more accurately image a desired location by accurately radiating X-rays toward an oral sensor.

Effects of the present disclosure are not limited to the aforementioned effects, and other effects not described above may be evidently understood by a person having ordinary knowledge in the art to which the present disclosure pertains from the following description.

DETAILED DESCRIPTION

Figure 1:
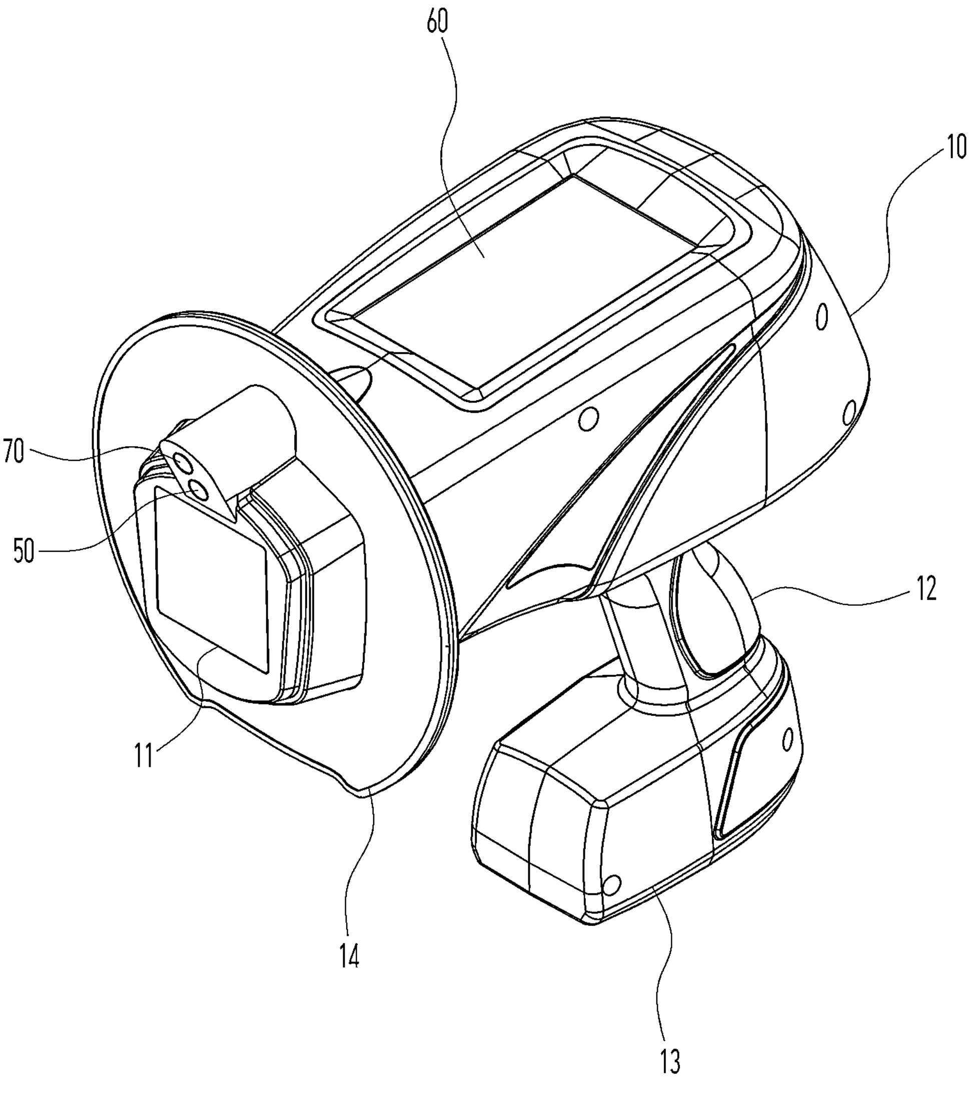
FIG. 1 is a perspective view of an outward appearance of a portable X-ray imaging device according to an embodiment of the present disclosure.

In embodiments of the present disclosure, the accompanied drawings may have been illustrated as exaggerated expressions for differentiation and clarity with a conventional technology and for convenience of the checking of a technology. In this process, the thicknesses of lines or the sizes of components illustrated in the drawings for the clarity of a description and for convenience' sake. Furthermore, terms to be described below have been defined by taking into consideration their functions in the present disclosure, and may be changed depending on a user or operator's intention or practice. Accordingly, such terms should be defined based on the overall contents of this specification. An embodiment is merely an exemplary item of a component that is presented in the claims of the present disclosure, and does not limit the range of rights of the present disclosure. The range of rights should be construed based on the technical spirit over the entire specification of the present disclosure.

In the entire specification, when it is described that a component "includes" another component, this means that the component does not exclude any other components, but may further include other components unless specially described to the contrary.

Furthermore, when it is described that a component is "connected to", "coupled to", or "combined with" the other component, this means that the component may be "directly connected to", "directly coupled to", or "directly combined with" the another component, or may be "indirectly connected to the another component through a third component", "indirectly coupled to the another component through a third component", or "indirectly combined with the another component through a third component". In contrast, when it is described that a component is "directly connected to", "directly coupled to", or "directly combined with" another component, it should be understood that a third component is not present between the two components.

Furthermore, when directional terms, such as "front", "rear", "upper", "lower", "left", "right", "one end", "the other end", and "both ends", are used, the terms are exemplarily used in relation to the orientations of the disclosed drawings, and should not be limitedly construed. When terms, such as "first" and "second", are used, the terms are terms for distinguishing between components and should not be limitedly construed.

In order to more clearly describe characteristic of embodiments of the present disclosure, a detailed description of contents that have been widely known to a person having ordinary knowledge in the art to which the following embodiments pertain are omitted. Furthermore, a detailed description of a part not related to the description of the embodiments in the drawings is omitted.

Embodiments of the present disclosure are described in detail with reference to the accompanying drawings.

Figure 2:
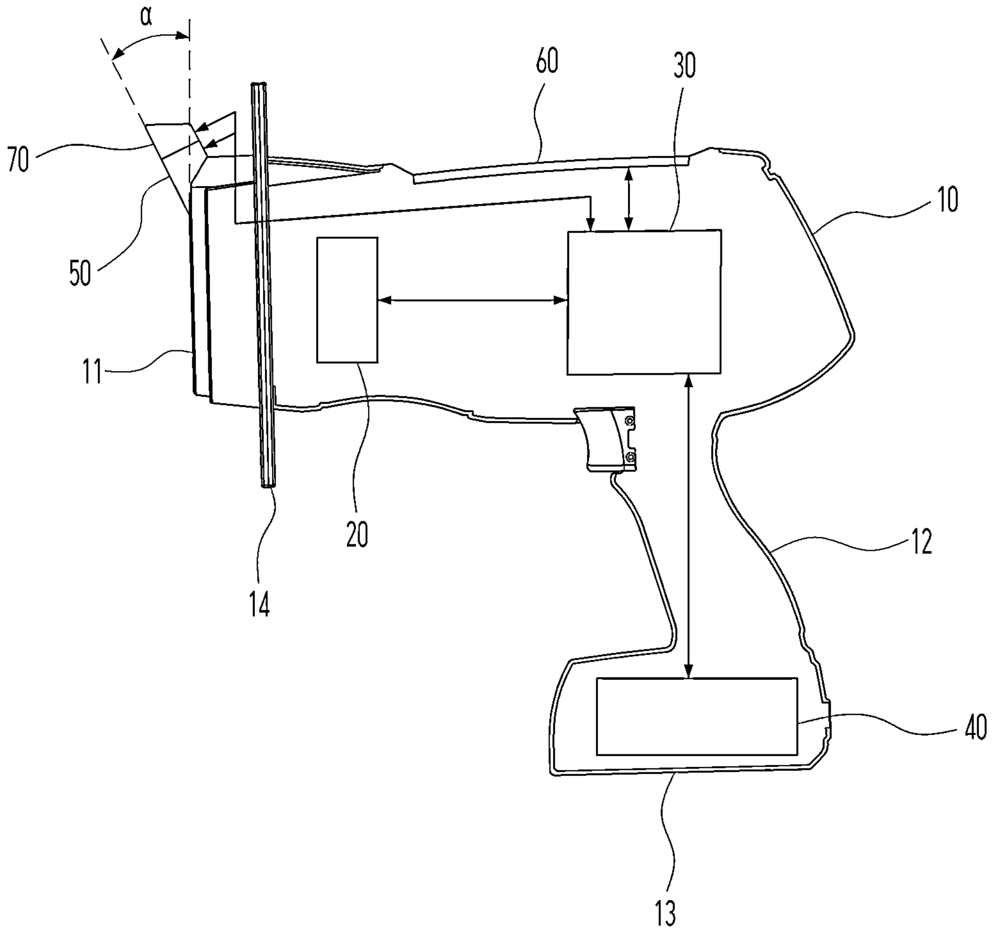
FIG. 2 is a schematic construction diagram of the portable X-ray imaging device according to an embodiment of the present disclosure.
Figure 3:
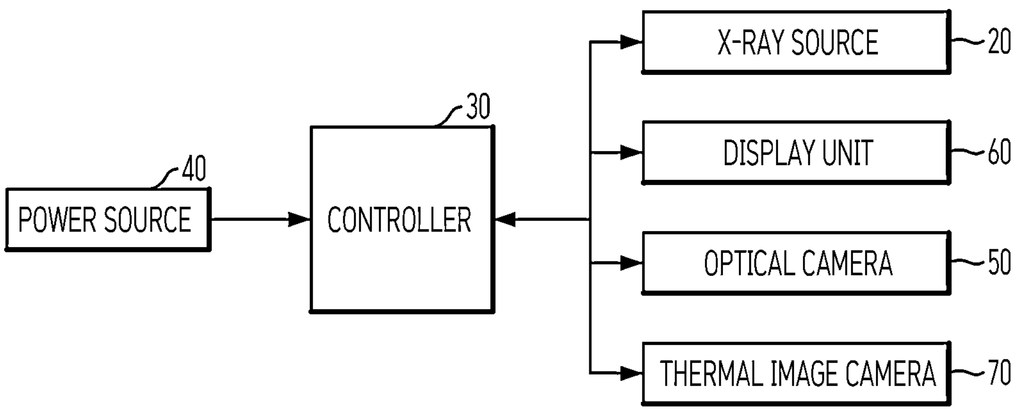
FIG. 3 is a block diagram illustrating a construction of the portable X-ray imaging device according to an embodiment of the present disclosure.
Figure 4:
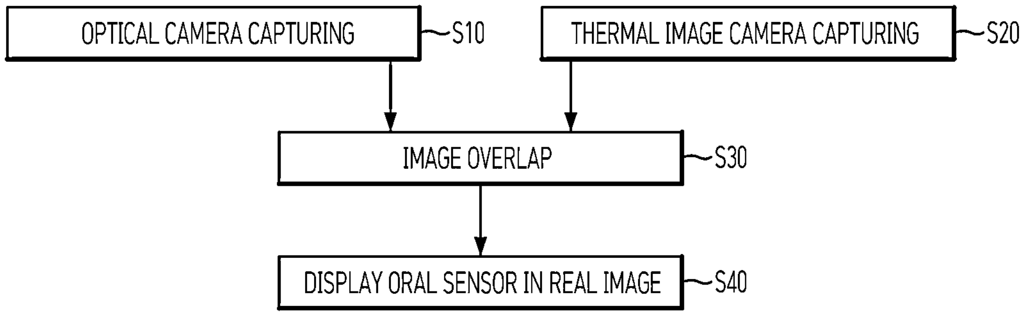
FIG. 4 is a control flowchart of a controller, that is, one component of the portable X-ray imaging device according to an embodiment of the present disclosure.
Figure 5:
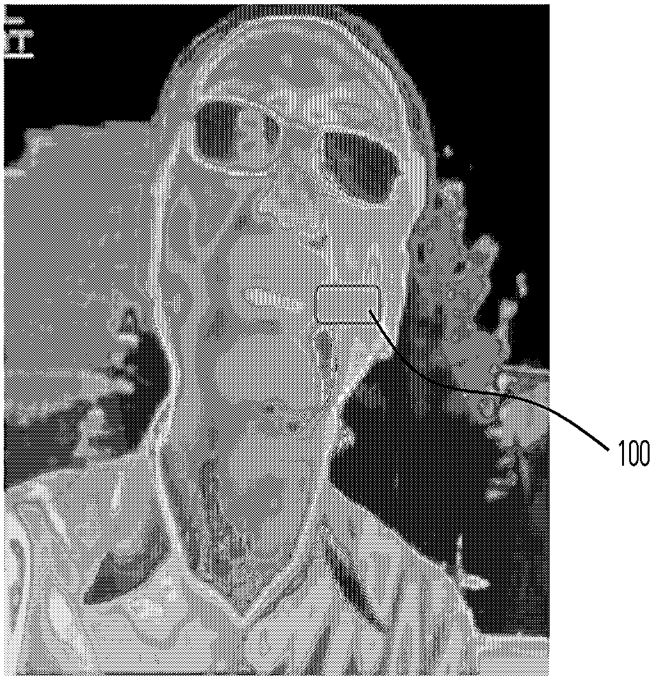
FIG. 5 is an exemplary diagram of a thermal image captured by a thermal image camera, that is, one component of the portable X-ray imaging device according to an embodiment of the present disclosure.

FIG. 1 is a perspective view of an outward appearance of a portable X-ray imaging device according to an embodiment of the present disclosure. FIG. 2 is a schematic construction diagram of the portable X-ray imaging device according to an embodiment of the present disclosure. FIG. 3 is a block diagram illustrating a construction of the portable X-ray imaging device according to an embodiment of the present disclosure. FIG. 4 is a control flowchart of a controller, that is, one component of the portable X-ray imaging device according to an embodiment of the present disclosure. FIG. 5 is an exemplary diagram of a thermal image captured by a thermal image camera, that is, one component of the portable X-ray imaging device according to an embodiment of the present disclosure.

Referring to FIGS. 1 to 5, the portable X-ray imaging device according to an embodiment of the present disclosure includes an X-ray source 20, an optical camera 50, a thermal image camera 70, a display unit 60, and a controller 30. The X-ray source 20 and the controller 30 are installed within a main body 10 of the portable X-ray imaging device. The optical camera 50, the thermal image camera 70, and the display unit 60 are installed outside or inside the main body 10, or are installed in the state in which the optical camera 50, the thermal image camera 70, and the display unit 60 have been exposed to an outside surface of the main body 10.

As described above, the main body 10 is a major part of the portable X-ray imaging device, and provides places where the components are installed on the inside and outside thereof. A handle part 12 that slantly protrudes at a predetermined angle is disposed at the bottom of the main body 10 thereunder. A power source part 13 in which a power source 40, that is, a battery, is embedded is extended and disposed at the bottom of the handle part 12. The battery may be charged by being connected to an external power source.

Furthermore, an X-ray radiation window 11 configured to transmit X-rays, but prevent an alien substance from penetrating an internal space of the main body 10 is provided at the front end of the main body 10. The X-ray radiation window 11 may be made of a semi-transparent or opaque plastic material.

Furthermore, a shielding plate 14 having a structure in which the shielding plate protrudes in an external direction of the main body 10 from the entire circumference of the main body 10 and having an approximately disc form is disposed in the rear of the front end of the main body 10 at a predetermined distance from the front end. The shielding plate 14 functions to block X-rays that are backward scattered toward a user when the X-rays are radiated.

The X-ray source 20 is installed within the main body 10, and is installed in the state in which the X-ray source faces the X-ray radiation window 11.

The X-ray source 20 is for generating X-rays. An X-ray source using an X-ray tube method or a thermal electron source method may be applied to the X-ray source 20. A detailed construction of the X-ray source 20 is not the subject matter of the present disclosure, and thus a detailed description and drawing thereof is omitted.

An operation of the X-ray source 20 may be controlled by the controller 30. However, a user may deliver a control command to the controller 30 by selecting a menu that is displayed on the display unit 60 by using a screen touch method or a method of manipulating a button (not illustrated) or a Jog dial (not illustrated).

The optical camera 50 is a camera for obtaining an image of a subject by detecting light that is reflected by the subject, and may use a charge-coupled device (CCD) or a complementary metal-oxide semiconductor (CMOS) as an image sensor. The image sensor converts light incident on the camera into a digital signal. The digital signal may be transmitted to the display unit 60 through the controller 30 or directly and then displayed in the form of an image. The image is a color real image (i.e., an image of an outward appearance of the subject, which has been captured without any change). That is, the optical camera 50 images a shape of the face of a patient in the same way as a user sees the shape of the face of the patient with the naked eye. A corresponding image may be displayed on the display unit 60.

The thermal image camera 70 is a camera for constructing an image by visualizing infrared rays (or heat rays) that are emitted by a subject. An infrared sensor is used in the thermal image camera 70. The thermal image camera 70 may capture an image of an object regardless of whether light is present or not, and may also capture an image of an object behind various obstacles which cannot be seen with the naked eye.

Thermal image data that are imaged by the thermal image camera 70 may be transmitted to the display unit 60 through the controller 30 or directly, and may be displayed in the form of a thermal image.

FIG. 5 is a thermal image of the face of a patient who has an oral sensor 100 in his or her mouth. The oral sensor 100 has a relatively lower temperature than the face of a patient, and is thus displayed in the state in which the oral sensor is not seen in a real image, but can be clearly identified in a thermal image.

As illustrated in FIGS. 1 and 2, the optical camera 50 and the thermal image camera 70 are installed on the circumference of the end of the main body 10 on one side thereof. It is preferred that for the matching of directivity (=upper, lower, left, and right sides of an image) between a captured X-ray image and a real image or a thermal image, the optical camera 50 and the thermal image camera 70 are installed in an upper central part or lower central part of the circumference of the end of the main body 10.

Furthermore, it is preferred that the optical camera 50 and the thermal image camera 70 are installed to be adjacent to each other so that in images captured by the optical camera 50 and the thermal image camera 70, image angles of a subject (i.e., the face of a patient) and the sizes of the captured images are identical with each other as much as possible without a correction. In the illustrated example, the optical camera 50 has been disposed on the lower side of the circumference of the end of the main body 10 and the thermal image camera 70 has been installed to be adjacent to the optical camera 50 on the upper side thereof, but the upper and lower position relation between the optical camera 50 and the thermal image camera 70 may be reversed.

Furthermore, the optical camera 50 and the thermal image camera 70 may be installed to be adjacent to each other left and right at an upper central part or lower central part of the circumference of the end of the main body 10.

Furthermore, the optical camera 50 and the thermal image camera 70 have an installation angle α that is forward inclined at a predetermined angle with respect to the same plane as the X-ray radiation window 11. That is, the optical camera 50 and the thermal image camera 70 are installed in the state in which the optical camera 50 and the thermal image camera 70 have been forward inclined at the installation angle α with respect to a surface perpendicular to a direction in which the X-ray source 20 radiates X-rays. Accordingly, the center of the area (or range) in which the X-ray source 20 radiates X-rays and the center of an image area (or range) of the optical camera 50 and the thermal image camera 70 can be matched without a correction, or the amount of corrections can be minimized.

The installation angle α at which the optical camera 50 and the thermal image camera 70 are bent forward may properly set within a range of more than 0° to less than 30°. When the installation angle α is 0°, image directions of the X-ray radiation direction and the optical camera 50 and the thermal image camera 70 are parallel to each other. Accordingly, there is no correction effect for making the center of the area (or range) in which the X-ray source 20 radiates X-rays and the center of the image area (range) of the optical camera 50 and the thermal image camera 70. When the installation angle α is 30° or more, a difference between the direction to which the front of the main body 10 is directed and the image directions of the optical camera 50 and the thermal image camera 70 is greatly widened because the angle at which the optical camera 50 and the thermal image camera 70 are bent forward is excessive. Accordingly, when the portable X-ray imaging device is used, a feeling of a separation between a part that is felt by a user and that is to be imaged and a part that is actually imaged is increased.

The display unit 60 is installed at the top of the main body 10. The display unit 60 is a common color screen, such as a liquid crystal display (LCD) or organic light emitting diodes (OLED). Operation menus for using the portable X-ray imaging device are basically displayed on the display unit 60. As described above, the operation menus may be selected by manipulating a button or a Jog dial that is separately provided. Furthermore, the operation menus may be selected by directly touching a touch screen because the display unit 60 is formed of the touch screen.

The display unit 60 may receive image data from the optical camera 50 and the thermal image camera 70 directly or through the medium of the controller 30, and may display a real image and a thermal image.

Furthermore, the display unit 60 may display an overlap image of a real image and a thermal image which will be described hereinafter.

The controller 30 controls overall operations of the X-ray source 20, the optical camera 50, the thermal image camera 70, and the display unit 60 in response to the selection of an operation menu (i.e., a manipulation of the button or the Jog dial or selection using a display screen touch method) by a user.

Furthermore, the controller 30 performs the following control process.

As illustrated in FIG. 4, the controller 30 performs an optical camera capturing step S10, a thermal image camera capturing step S20, and an image overlap step S30. Furthermore, the controller 30 may further perform a step S40 of displaying the oral sensor 100 in a real image after the image overlap step S30.

The optical camera capturing step S10 is a step of capturing, by the controller 30, a real image of the face of a patient by using the optical camera 50. The data or the real image of the face of the patient, which is obtained in this step, may be transmitted to the display unit 60 directly or through the controller 30, may be displayed in the form of a real image, and may be stored in memory that is one component of the controller 30.

The thermal image camera capturing step S20 is a step of capturing, by the controller 30, a thermal image of the face of the patient by using the thermal image camera 70. The data of the thermal image of the face of the patient, which is obtained in this sep, may be transmitted to the display unit 60 directly or through the controller 30, may be displayed in the form of a thermal image, and may be stored in the memory.

The order in which the optical camera capturing step S10 and the thermal image camera capturing step S20 are performed may be reversed, or the optical camera capturing step S10 and the thermal image camera capturing step S20 may be simultaneously performed.

The image overlap step S30 is a step of overlapping, by the controller 30, the real image and thermal image of the face of the patient by using the data of the real image and the data of the thermal image stored in the memory. In overlapping the real image and the thermal image in the image overlap step S30, in order to accurately matching the real image and the thermal image, a method of matching a plurality of points that correspond to each other in the real image and the thermal image is used. For example, three points corresponding to a central point between both eyes and the peak of the nose of the patient in each of the real image and the thermal image may be determined. When the three points of the real image and the three points of the thermal image are matched, the real image and the thermal image can be accurately overlapped. In this case, the same results may be obtained by matching the triangle of specific three points of the real image and the triangle of specific three points of the thermal image.

A composite image that is generated by the overlapping of the real image and the thermal image as described above includes a shape of the face of the patient and the oral sensor 100. The composite image is displayed on the display unit 60.

Accordingly, a user may check the location of the oral sensor 100 in the real image of the face of the patient, which is displayed on the display unit 60. In this case, the user can feel a more sense of reality because the face of the patient is displayed similarly to the real image in the displayed overlap image compared to the existing thermal image.

The user can more accurately image a portion to be captured by adjusting the posture of the portable X-ray imaging device so that the oral sensor 100 is placed at the center of a screen in the state in which the overlapped composite image has been displayed on the display unit 60 as described above and then performing X-ray imaging in the state in which the oral sensor 100 has been placed at the center of the screen.

A phenomenon in which the identifiability of the oral sensor 100 is reduced when the real image and the thermal image are simply overlapped can be prevented by reducing resolution of the real image and the thermal image when the real image and the thermal image are overlapped as described above and then overlapping the real image and the thermal image.

Furthermore, the step S40 of displaying the oral sensor in the real image may be further performed after the image overlap step S30. The step S40 of displaying the oral sensor in the real image includes restoring the resolution of the real image and the thermal image to their original state and making transparent the remaining part of the thermal image except only the part of the oral sensor 100. Alternatively, the identifiability of the oral sensor 100 can be improved by displaying the part of the oral sensor 100 in a specific color that is separately selected or displaying the outer contour (i.e., a line that is displayed along the edge of a shape of the oral sensor) of the oral sensor 100 along with the displaying of the specific color.

In such a case, since the oral sensor 100 is more clearly displayed in the face of the patient displayed in the real image, the user can feel a more sense of reality in an image displayed on the display unit 60 and also more accurately check the location of the oral sensor 100 in the face of the patient, compared to a case in which the real image and the thermal image are overlapped without any change.

FIG. 4 illustrates that the step S40 of displaying the oral sensor in the real image is performed after the image overlap step S30. However, the step S40 of displaying the oral sensor in the real image may be understood as an embodiment of the image overlap step S30.

A user can perform X-ray imaging at a more accurate location by using the portable X-ray imaging device according to an embodiment of the present disclosure because the oral sensor can be displayed in a real image of the face of a patient as described above.

As described above, the present disclosure has been described with reference to the embodiments illustrated in the drawings, but this is merely exemplary. It should be understood that various modifications and other equivalent embodiments are possible based on common knowledge in the art to which a corresponding technology pertains. Accordingly, the true technical range of protection of the present disclosure is based on the claims to be described hereinafter and should be determined based on the aforementioned detailed contents of the present disclosure.

INDUSTRIAL APPLICABILITY

The present disclosure relates to the portable X-ray imaging device, and may be used in the industrial field related to a portable X-ray imaging device including a display unit on which a captured real image and thermal image can be displayed.

[Description of reference numerals]

| | |
|---|---|
| 10: main body | 11: X-ray radiation window |
| 12: handle part | 13: power source part |
| 14: shielding plate | 20: X-ray source |
| 30: controller | 40: power source |
| 50: optical camera | 60: display unit |
| 70: thermal image camera | |

What is claimed is:

1. A portable X-ray imaging device comprising:
   - a main body in which an X-ray radiation window has been disposed at a front end thereof;
   - an X-ray source installed within the main body;
   - an optical camera installed on an outer circumference of the front end on one side of the main body and configured to capture a real image of a subject;
   - a thermal image camera installed adjacently to the optical camera and configured to capture a thermal image of the subject;
   - a display unit installed on a top of the main body and configured to display the real and thermal images captured by the optical camera and the thermal image camera; and
   - a controller configured to control operations of the X-ray source, the optical camera, the thermal image camera, and the display unit.

2. The portable X-ray imaging device of claim 1, wherein the optical camera and the thermal image camera are installed at an upper center of the circumference of the front end of the main body.

3. The portable X-ray imaging device of claim 2, wherein the optical camera and the thermal image camera are installed in a state in which the optical camera and the thermal image camera have an installation angle $\alpha$ at which the optical camera and the thermal image camera have been forward inclined with respect to a surface perpendicular to a direction in which the X-ray source radiates X-rays.

4. The portable X-ray imaging device of claim 3, wherein the installation angle $\alpha$ is in a range of more than 0° to less than 30°.

5. The portable X-ray imaging device of claim 1, wherein the display unit displays the real image captured by the optical camera without any change.

6. The portable X-ray imaging device of claim 1, wherein the display unit displays the thermal image captured by the thermal image camera without any change.

7. The portable X-ray imaging device of claim 1, wherein:
   - the controller generates an overlap image by overlapping the real image captured by the optical camera and the thermal image captured by the thermal image camera, and
   - the display unit displays the overlap image.

8. The portable X-ray imaging device of claim 7, wherein:
   - the optical camera generates data of the real image obtained by capturing a face of a patient who has an oral sensor in his or her mouth,
   - the thermal image camera generates data of the thermal image obtained by capturing the face of the patient who has the oral sensor in his or her mouth,
   - the controller generates the overlap image in which the oral sensor has been displayed in the real image of the face of the patient by overlapping the real image of the face of the patient and the thermal image of the face of the patient, based on the data of the real image and the data of the thermal image which have been obtained by capturing the face of the patient who has the oral sensor in his or her mouth, and
   - the display unit displays the overlap image in which the oral sensor has been displayed in the real image of the face of the patient.

9. The portable X-ray imaging device of claim 8, wherein the controller overlaps the real image of the face of the patient and the thermal image of the face of the patient after reducing resolution of the real image and the thermal image.

10. The portable X-ray imaging device of claim 8, wherein the controller overlaps the real image of the face of the patient and the thermal image of the face of the patient, in a way to specify a plurality of points in the real image of the face of the patient, specify a plurality of identical points corresponding to the plurality of specified points in the thermal image of the face of the patient, and match the plurality of points of the real image and the plurality of points of the thermal image.

11. The portable X-ray imaging device of claim 10, wherein the plurality of points is three points corresponding to a central point between both eyes of the patient and a peak of a nose of the patient.

12. The portable X-ray imaging device of claim 8, wherein the controller overlaps the real image in an original state and the thermal image a remaining part of which has been processed to be transparent except a part of the oral sensor in the original state.

13. The portable X-ray imaging device of claim 12, wherein the controller displays the part of the oral sensor in a specific color.

14. The portable X-ray imaging device of claim 12, wherein the controller displays an outer contour in the part of the oral sensor.

* * * * *